United States Patent [19]
Mendius

[11] Patent Number: 6,027,470
[45] Date of Patent: Feb. 22, 2000

[54] PUNCTUM PLUG AND METHOD FOR INSERTING THE SAME INTO THE PUNCTUAL OPENING

[75] Inventor: Richard W. Mendius, Collierville, Tenn.

[73] Assignee: Eagle Vision, Inc., Memphis, Tenn.

[21] Appl. No.: 09/095,194

[22] Filed: Jun. 10, 1998

[51] Int. Cl.$^7$ ..................................................... A61M 5/00
[52] U.S. Cl. ..................................................... 604/8; 604/9
[58] Field of Search ................................. 604/294, 337, 604/338, 8, 9; 623/4

[56] References Cited

U.S. PATENT DOCUMENTS

| | | | |
|---|---|---|---|
| 3,949,750 | 4/1976 | Freeman | 128/260 |
| 4,915,684 | 4/1990 | MacKeen et al. | 604/8 |
| 4,959,048 | 9/1990 | Seder et al. | 604/9 |
| 5,171,270 | 12/1992 | Herrick | 623/11 |
| 5,283,063 | 2/1994 | Freeman | 424/427 |
| 5,334,137 | 8/1994 | Freeman | 604/8 |
| 5,417,651 | 5/1995 | Guena et al. | 604/8 |
| 5,423,777 | 6/1995 | Tajiri | 604/294 |
| 5,601,553 | 2/1997 | Trebing et al. | 606/61 |
| 5,645,565 | 7/1997 | Rudd et al. | 606/213 |
| 5,723,005 | 3/1998 | Herrick | 604/8 |

*Primary Examiner*—Michael Buiz
*Assistant Examiner*—Julian W. Woo
*Attorney, Agent, or Firm*—David P. Gordon; David S. Jacobson; Thomas A. Gallagher

[57] ABSTRACT

A punctum plug includes a proximal head, a distal body, and a shaft between the head and the body. The head and shaft are provided with a bore to facilitate insertion of the plug through the punctal opening with an insertion tool. According to one aspect of the invention, the head is provided with a lower portion having a frustoconical shape which, in situ, reduces the external profile of the head, without sacrificing the thickness of the head. Preferably, the head includes peripheral upper and lower surfaces which are both non-orthogonal to the longitudinal axis of the shaft, and a more central upper surface which is generally orthogonal to the longitudinal axis of the shaft. According to a second aspect of the invention, the head has an oblong cross-section such that long and short lateral dimensions are defined across the head. According to a third aspect of the invention, at least a proximal portion of the shaft is provided with an oblong cross-section. The exterior shape of the head, and the oblong shape of the head and waist provide a punctum plug which has an improved anatomical fit in the vertical punctum and at the punctal opening, and thereby minimizes contact between the head of the plug and the conjunctiva of the eye, and thereby reduces eye irritation.

49 Claims, 4 Drawing Sheets

PUNCTUM PLUG AND METHOD FOR INSERTING THE SAME INTO THE PUNCTUAL OPENING

BACKGROUND OF THE INVENTION

1. Field of the Invention

This invention relates broadly to medical canalicular inserts. More particularly, this invention relates to canalicular plugs which are placed into the punctal opening and vertical punctum to prevent lacrimal fluid from flowing through the lacrimal duct.

2. State of the Art

A variety of eye problems are related to an insufficient volume of tears on the surface of the eyes. The most common is keratoconjunctivitis sicca, also known as dry eyes. Contact lens problems are also often provoked by a lack of tear volume. A common cause for the insufficient tear volume is the drainage of tear fluid through the punctal opening of the nasal lacrimal duct and into the nasal passage, thereby removing the fluid from where it is needed at the eye surface. Furthermore, drainage of tear fluid through the nasal lacrimal duct into the nasal passage is believed to be the cause or associated with several additional problems such as post nasal drip, sinusitis, allergies, headaches, and snoring.

A number of methods for closing the punctal opening have been used to prevent drainage of tears through the nasal lacrimal duct, including suturing, laser sealing, and plugging. Plugging with a canalicular plug such as a punctum plug or a lacrimal plug is the least severe solution, is relatively inexpensive, and is being performed with increasing frequency.

Figures 1, 2, 3:
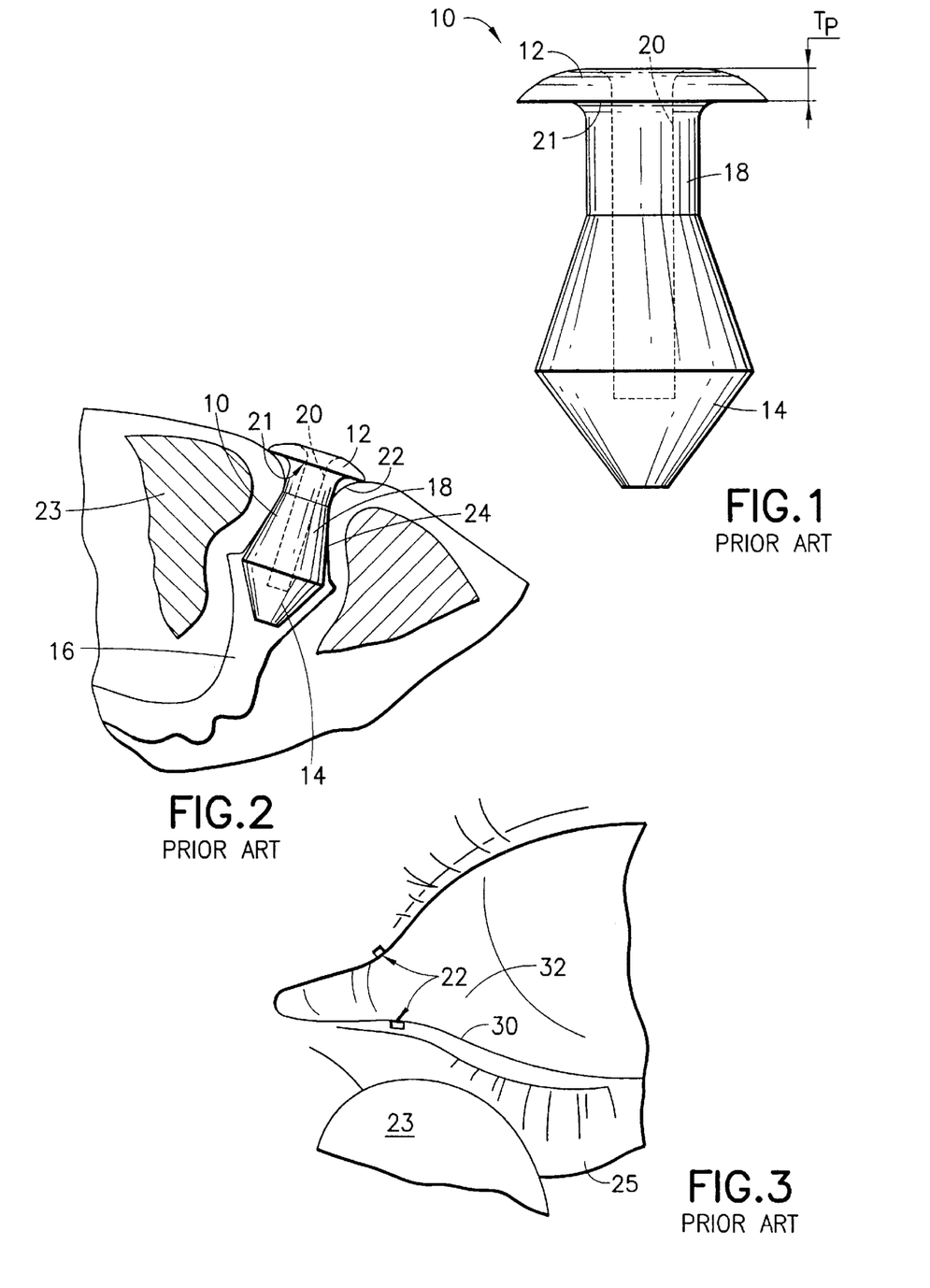
FIG. 1 is a side elevation of a prior art punctum plug.
FIG. 2 is a side elevation of the prior art punctum plug of FIG. 1 inserted into the punctum of a patient.
FIG. 3 is a partial section view of an eye.

Referring to prior art FIGS. 1 and 2, a punctum plug 10 typically is an elongate member having a relatively large dome-shaped proximal head 12, a relatively large distal body 14 for occluding the lacrimal duct 16, and a relatively narrower cylindrical shaft 18 therebetween. The plug 10 is usually provided with a proximal axial bore 20 for receiving an insertion tool. In addition, the head 12 has a material thickness $T_P$ about the bore 20 which is of sufficient thickness to prevent the head from pushing through the punctal opening 22 and also provides enough mass to permit lifting of the head for removal of the plug without ripping the head. The head 12 is also provided with a peripheral lower surface 21 which is substantially orthogonally oriented to the bore 20 of the plug 10.

Figure 4A:
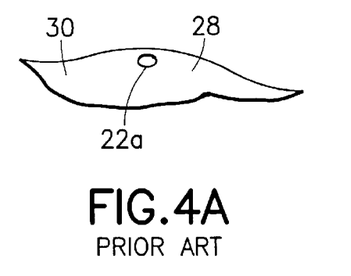
FIGS. 4A and 4B are section views of punctal openings.
Figure 4B:
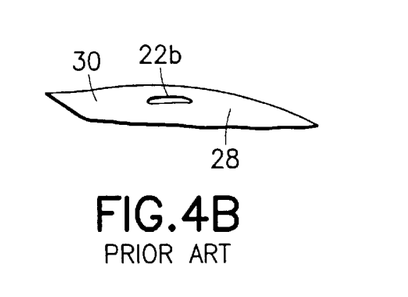
Figure 5:
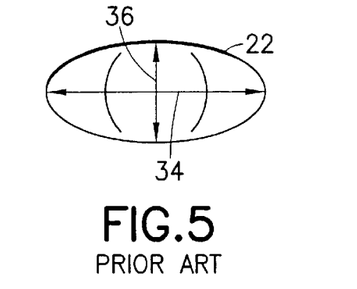
FIG. 5 is a top view of a punctal opening.

Referring to prior art FIGS. 2 and 3, in the punctum plug insertion procedure, the physician positions an insertion tool in the bore 20 of the plug, and, while a physician uses a finger 23 to hold the lower lid 25 open, the body 14 of the plug is directed at the upper or lower punctal opening 22 of the patient. Depending on the anatomy of the patient, the punctal opening 22 is either exposed on the surface 28 of the lid margin 30 or somewhat introverted on the lid margin 30 and lying against the surface of the conjunctiva 32 of the eye. Referring to FIGS. 4A and 4B, the punctal opening 22 has a funnel-like shape which may be substantially circular (FIG. 4A at 22a) or, more commonly, slit-like (FIG. 4B at 22b). When not substantially circular, the opening 22 has a relatively long axis 34 and a relatively short axis 36, with dimensions varying on an individual patient basis (FIG. 5). The long axis 34, where existing, always lies parallel to the posterior lid margin 30 and parallel to the surface of the conjunctiva 32 of the eye.

Referring back to prior art FIG. 2, force is applied to the insertion tool to move the body 14 of the plug 10 through the punctal opening 22 (constricted by the punctal ring 23), the vertical punctum 24, and into the lacrimal duct 16 such that the shaft 18 rests in the vertical punctum 24. The plug 10 is fully inserted when the head 12 seats over and against the punctal opening 22, the shaft 16 rests within the vertical punctum 24, and the body 14 lies within the vertical punctum or other portion of the lacrimal duct 16. Once the plug 10 is fully inserted in the vertical punctum and lacrimal duct, the insertion tool is removed. The punctum plug then operates to block the passage of tear fluid and thereby retain tear fluid at the surface of the eye. Lacrimal plugs which are placed entirely within the lacrimal duct (and below the punctal opening) are also known.

While the use of punctum plugs has generally provoked little patient criticism as to effectiveness and comfort, the most common complaint to physicians relates to the head portion of the punctum plug contacting and irritating the conjunctiva of the eye. There are various reasons why the head contacts the conjunctiva, but most involve individual punctal anatomy and plug size. In particular, the shape of the head and shaft portions of the punctum plug, which have not been substantially changed since U.S. Pat. No. 3,949,750 to Freeman for the original punctum plug device, is believed by the inventor to be the cause, as the dome shaped head and cylindrical shaft do not have satisfactory fit about and within the anatomical structure at the punctal opening and vertical punctum, respectively.

SUMMARY OF THE INVENTION

It is therefore an object of the invention to provide a punctum plug which occludes the flow of tears through the punctum and lacrimal duct.

It is another object of the invention to provide a punctum plug which has a head portion which minimizes contact with the conjunctiva of the eye when the plug is in situ in the punctum.

It is also an object of the invention to provide a punctum plug having a head portion which is designed for an excellent anatomical fit with the structure of the punctal opening.

It is an additional object of the invention to provide a punctum plug having a shaft portion which is designed for optimal anatomical fit within the structure of the vertical punctum.

In accord with these objects which will be discussed in detail below, a punctum plug is provided which generally includes a proximal head, a distal body, and a shaft between the head and the body. The proximal end of the plug is provided with a bore to facilitate insertion of the plug through the punctal opening with an insertion tool. According to one aspect of the invention, the head is provided with a lower portion having a frustoconical shape which, in situ, reduces the external profile of the head (i.e., the height of the portion of the head which rises above the punctal opening), without sacrificing the thickness of the head. More particularly, the head preferably includes a lower surface, and an upper surface having a planar or concave central portion about the bore and a peripheral portion about the central portion. The lower surface is angled relative to a plane extending orthogonally through a longitudinal axis of the shaft. The central portion of the upper surface extends relatively parallel to the plane or is slightly concave. According to another aspect of the invention, at least one of the head and a portion of the shaft is provided with an oblong cross-section such that the cross-section has long and short axes. According to one preferred embodiment of the shaft of the plug, only a proximal portion of the shaft includes an oblong cross-section, while a distal portion of the shaft has a circular cross-section, preferably flaring toward the body.

The frustoconical shape of the lower portion of the head and the oblong cross-sectionally shaped head and/or waist provide a punctum plug which has an improved anatomical fit in the vertical punctum and at the punctal opening. The head design permits the head to nest relatively deep in the punctal opening, as the head shape closely approximates the anatomy of the opening. The head design, however, still maintains a desired thickness and strength which inhibits the head from being pushed past the punctal ring and which permits removal of the plug by grasping the head. In addition, the waist of the punctum plug more closely approximates the anatomy of the vertical punctum. Furthermore, according to the method of the invention, the long axes of the head and/or shaft are positioned parallel to the surface of the conjunctiva, while the respective short axes are positioned at a right angle thereto. As a result, the punctum plug of the invention, in situ in a patient, is less likely to come into contact with the conjunctiva of the eye and result in eye irritation.

Additional objects and advantages of the invention will become apparent to those skilled in the art upon reference to the detailed description taken in conjunction with the provided figures.

BRIEF DESCRIPTION OF THE DRAWINGS

Prior art

Prior art

Prior art

Prior art

Prior art

DETAILED DESCRIPTION OF THE PREFERRED EMBODIMENTS

Figure 6:
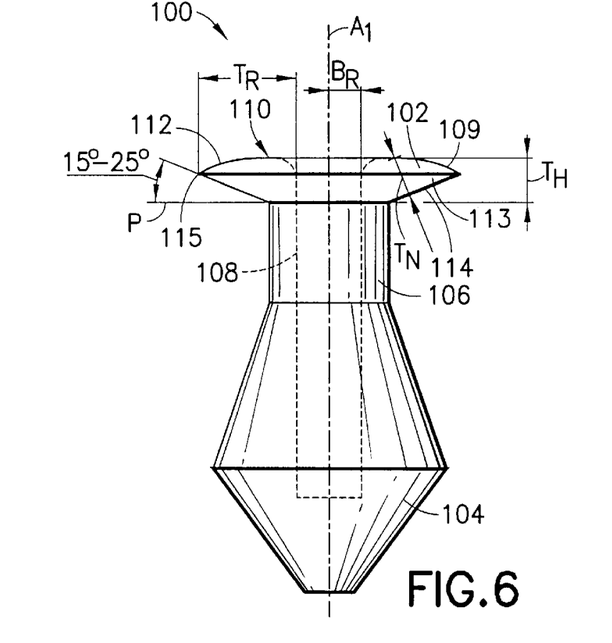
FIG. 6 is a side elevation of a first embodiment of the punctum plug of the invention.

Turning now to FIG. 6, a first embodiment of a punctum plug 100 according to the invention is shown. The punctum plug includes a proximal head 102, a distal body 104, and a shaft 106 between the head 102 and the body 104. The proximal end of the plug (generally the head 102 and shaft 106) is provided with a bore 108 to facilitate insertion of the plug through the punctal opening with an insertion tool. The shaft 106 may be cylindrical in shape or, as described below with respect to a second embodiment of the invention, may be provided with an oblong cross-section. The body 104 may be provided with substantially any shape known in the art. For example, amongst others, the distal bodies disclosed in U.S. Pat. Nos. 3,949,750, 5,283,063, 5,334,137, all to Freeman, and U.S. Pat. No. 5,417,651 to Guena et al., which are hereby incorporated by reference herein in their entireties, may be used. The plug is preferably molded from a silastic material, e.g., silicon.

According to the invention, the head 102 includes an upper surface 109 with a preferably substantially planar central portion 110 and a peripheral portion 112, and a lower portion 113 with a lower surface 114. The lower surface 114 is angled toward the upper surface 109, preferably at an angle of approximately 15° to 25° relative to a plane P extending laterally through the intersection of the head 102 and the shaft 106. The lower portion 113 is thereby provided with a frustoconical shape. The peripheral portion 112 of the upper surface 109 preferably curves (smoothly curves or angles) downward (toward plane P) to meet the lower surface 114 at an edge 115, i.e., the peripheral portion is preferably convexly curved.

Referring to FIG. 6, the ratio of the radial thickness $T_R$ of the material of the head 102 to the radius $B_R$ of the bore 108, in a direction perpendicular to the axis $A_1$ of the plug, is preferably at least one to one, and preferably substantially greater than one to one (e.g., approximately three to one) at the edge 115 of the juncture of the peripheral portion 112 of the upper surface and the lower surface 114. In addition, the radial thickness $T_R$ changes in a proximal direction, increasing in thickness up to the juncture of the lower and upper portions (i.e., through the radius extending through edge 115), and then decreasing in thickness from the juncture to the central portion 110 of the upper surface 109 of the head. Moreover, the thickness $T_N$ of the head in a direction normal to the lower surface 114 preferably changes over the head 102, decreasing from the juncture of the head and shaft to the edge 115. The vertical thickness $T_H$ of the plug material at the head 104 about the central bore 108 is substantially the same as or greater than the thickness $T_P$ of the prior art plug head 12 (as shown in FIG. 1), thus providing the head with sufficient strength for plug support and removal.

In situ, as will be described in more detail below with respect to FIG. 13, the frustoconical shape of the lower portion 113 of the head permits the head of the plug to seat relatively deep in the punctal opening. The profile of the head (i.e., the thickness of the portion of the head which rises above the punctal opening when the punctum plug is inserted in the punctum) is thereby reduced by approximately one-half relative to prior art punctum plug heads. However, as previously mentioned, the head thickness $T_H$ is comparable to the thickness $T_P$ of prior art heads, and head strength is not sacrificed.

Figure 7:
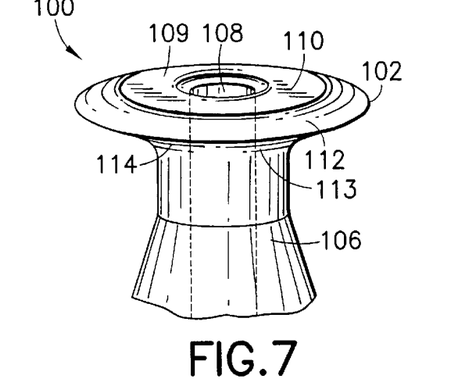
FIG. 7 is a partial top perspective view of the first embodiment of the punctum plug of the invention.
Figure 8:
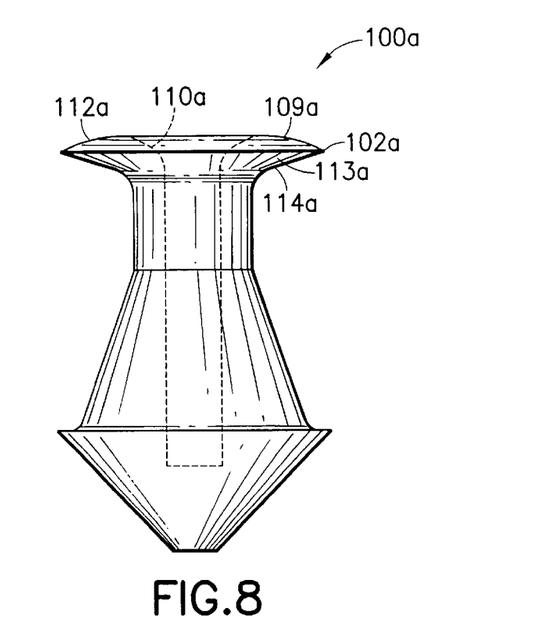
FIG. 8 is a side elevation of the first embodiment of the punctum plug of the invention, illustrating an alternate configuration of the upper surface of plug.
Figure 9:
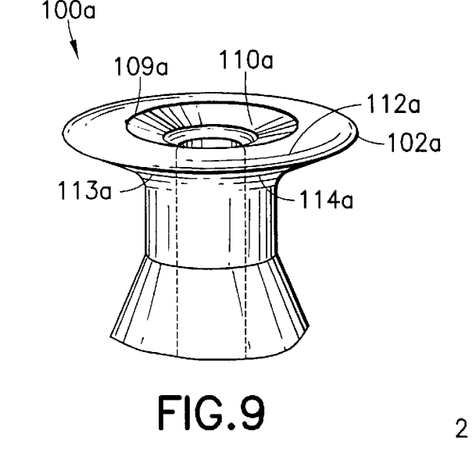
FIG. 9 is a partial top perspective view of the first embodiment of the punctum plug of the invention, illustrating the alternate configuration of the upper surface.

Turning now to FIGS. 8 and 9, according to an alternate configuration of the upper surface 109a of the head 102a of the first embodiment of the punctum plug 100a of the invention, the upper surface 109a has a generally concave central portion 110a and a peripheral portion 112a. The concave design sacrifices a small amount of head thickness, relative to the embodiments shown in FIGS. 6 and 7, in exchange for the plug, in situ, having a lower profile. In substantially all other respects, the plug shown in FIGS. 8 and 9 is preferably the same to the plug described with respect to FIGS. 6 and 7.

Figure 10:
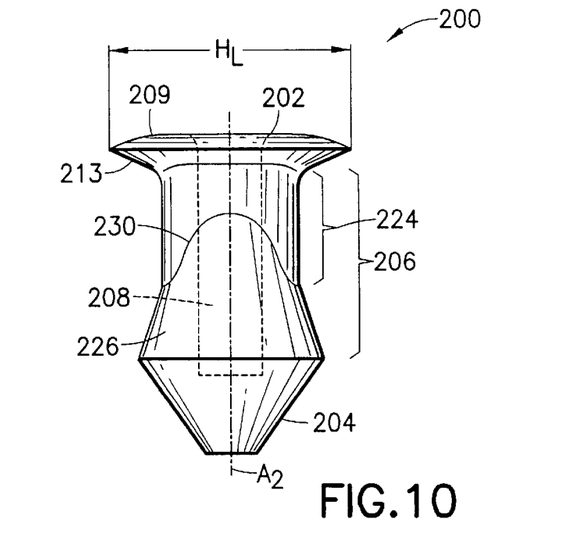
FIG. 10 is a first side elevation of a second embodiment of the punctum plug of the invention.
Figure 11:
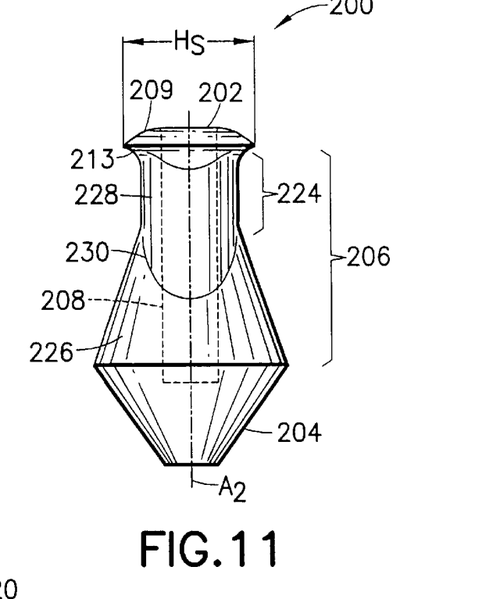
FIG. 11 is a second side elevation, orthogonal to the first side elevation, of the second embodiment of the punctum plug of the invention.
Figure 12:
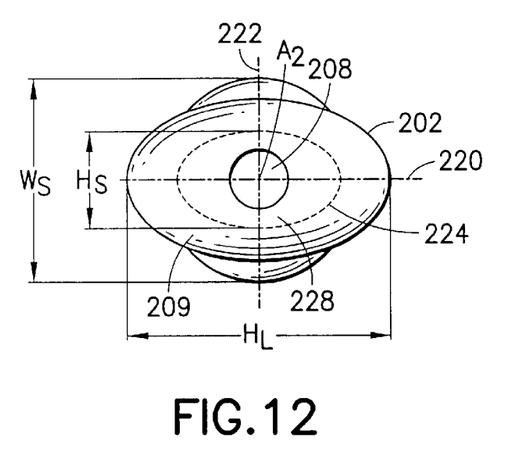
FIG. 12 is a top view of the second embodiment of the punctum plug of the invention.

Turning now to FIGS. 10 through 12, a second preferred embodiment of a punctum plug according to the invention (with like elements having numbers incremented by 100) is shown. The plug 200 includes a head 202, preferably substantially as described above with respect to the first embodiment (with a frustoconical lower portion 213 and a low profile upper surface 209), a shaft 206, and a body 204. A proximal bore 208 is provided in the plug about the longitudinal axis $A_2$ of the plug. According to a first preferred aspect of the second embodiment of the invention, the head 202 is provided with an oblong-shaped cross-section, e.g., an elliptical or other elongate closed-curve cross-section such that both a long lateral axis 220 having a first dimension $H_L$ across the head and a short lateral axis 222 (substantially perpendicular to the long lateral axis 220) having a second dimension $H_S$ across the head are defined. According to a second preferred aspect of the second embodiment of the invention, at least a proximal portion (waist) 224 of the shaft 206 of the plug 200 is provided with an oblong cross-section, preferably having a shape similar to the head, but smaller in size, with long and short lateral axes oriented in corresponding directions as the long and short lateral axes 220, 222 of the head 202. The size of the waist 224 relative to the bore 208 therethrough, especially surrounding the small axis $W_S$ of the waist, is large enough such that the wall 228 comprising the waist 224 has a minimum thickness which is structurally sufficient. The distal portion 226 of the shaft is preferably provided with a substantially circular cross-section and also preferably flares to meet the relatively larger body 204. The waist 224 and distal portion 226 of the shaft preferably have a smoothly transitioning intersection 230 which curves in three dimensions.

To insert the punctum plug into the punctal opening of a patient, an insertion tool is first placed into the bore of the plug and the plug is positioned at the punctal opening. The plug is inserted into the punctal opening, with the shorter lateral axes of the head and waist being oriented at approximately right angles to the surface of the conjunctiva, while the longer lateral axes are oriented parallel to the surface of the conjunctiva. By duplicating on the plug the oblong, slit-like shape of the punctal opening, this orientation is facilitated by the anatomy of the punctal opening and vertical punctum.

Figure 13:
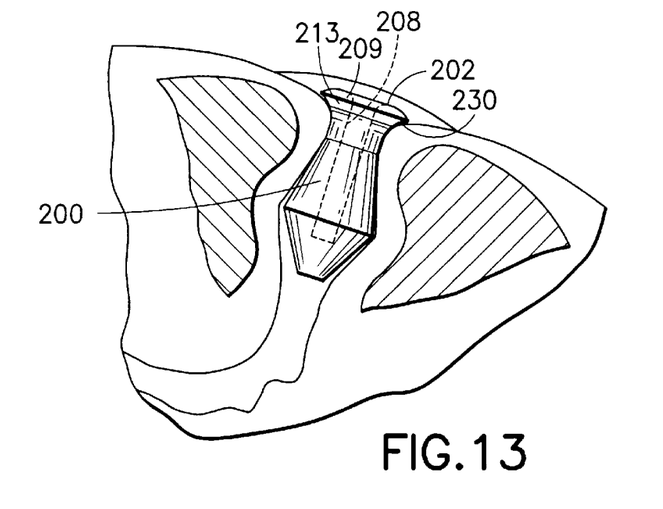
FIG. 13 illustrates the punctum plug of the invention inserted in a punctal opening.

Referring to FIG. 13, when incorporating the preferred aspects of the first embodiment of the invention in which the lower portion 213 of the head 202 has a frustoconical shape and the upper surface 209 has a low profile, the plug 200 is inserted through the punctal opening until the head 202 seats within the punctal opening 230 with only approximately one-half the height of the head exposed relative to prior art punctum plugs. As a result, the punctum plug of the second embodiment of the invention, in situ in a patient, is less likely to come into contact with the conjunctiva of the eye and result in eye irritation.

The plug embodiments may be provided in several sizes to provide satisfactory insertion into punctum of varying dimensions and to thereby occlude nasal lacrimal ducts. By way of example, and not by way of any limitation, the following dimensions are provided for one size of a punctum plug, for example, the plug described as the second embodiment of the invention as shown in FIGS. 10–12. The longer dimension $H_L$ across the head is approximately 0.040 inches and the shorter dimension $H_S$ across the head is approximately 0.022 inches. The lower surface of the head is angled at approximately 20° relative to the plane P. The waist of the shaft has a longer lateral dimension of 0.020 inches and a shorter lateral dimension of 0.014 inches. The diameter of the plug at the intersection of the shaft and the body is approximately 0.036 inches. The length of the plug from the proximal end of the head to the distal end of the body is approximately 0.050 inches.

There have been described and illustrated herein several embodiments of a punctum plug. While particular embodiments of the invention have been described, it is not intended that the invention be limited thereto, as it is intended that the invention be as broad in scope as the art will allow and that the specification be read likewise. Thus, while particular head and shaft portion have been disclosed, it will be appreciated that other combinations of the head and shaft portions can be used as well. For example, a circular head portion in combination with a waist having an oblong cross-section can be used. Furthermore while a particular range of preferred angles (15°–25°) of the lower surface of the head relative to plane P has been disclosed, it will be appreciated that other angles, preferably in the range of 5° to 55°, may likewise be provided to the lower surface. Moreover, while in one configuration of the invention, the central portion is described as being substantially planar, it will be appreciated that it is intended that "substantially planar" include the central portion being planar or having a slightly convex shape (i.e., a substantially flattened dome shape), such that a slightly convex shape provided to the head of a punctum plug, in combination with the other claimed limitations, does not escape the breadth of the invention claimed below. In addition, while only a proximal portion (waist) of the shaft is previously described as preferably having an oblong cross-section, it will be appreciated that substantially the entire length of the shaft may be provided with an oblong cross-section. It will therefore be appreciated by those skilled in the art that yet other modifications could be made to the provided invention without deviating from its spirit and scope as so claimed.

What is claimed is:

1. A punctum plug for insertion through the punctal opening of an eye, comprising:

a) a head portion having an upper surface and a lower surface, said upper surface having a substantially planar central portion and a substantially convex peripheral portion about said central portion; and b) a distal portion sized to be received at least partially through the punctal opening,
    said punctum plug defining a longitudinal axis, and
    said lower surface being angled relative to a first plane extending orthogonally through said longitudinal axis.

2. A punctum plug according to claim 1, wherein:
    said lower surface is angled approximately 15°–25° relative to said first plane.

3. A punctum plug according to claim 1, wherein:
    said head has a directionally normal thickness in a direction normal to said lower surface which changes along a length of said lower surface.

4. A punctum plug according to claim 3, wherein:
    said lower surface and said peripheral surface meet at a juncture, and said directionally normal thickness decreases toward said juncture.

5. A punctum plug according to claim 1, wherein:
    said central portion of said upper surface is substantially parallel to said first plane.

6. A punctum plug according to claim 1, wherein:
    said distal portion includes a distal body portion sized to be received through the punctal opening and a proximal shaft portion provided between said head portion and said body portion.

7. A punctum plug according to claim 1, wherein:

said head portion has an oblong cross-section perpendicular to said longitudinal axis.

8. A punctum plug according to claim 7, wherein:

said oblong cross-section is substantially elliptical in shape.

9. A punctum plug according to claim 1, wherein:

at least a portion of said distal portion has an oblong cross-section perpendicular to said longitudinal axis.

10. A punctum plug according to claim 1, wherein:

said plug is provided with a proximal bore substantially coaxial with said longitudinal axis.

11. A punctum plug according to claim 10, wherein:

said proximal bore tapers outwardly at a proximal portion of said head portion, said central portion surrounding said bore.

12. A punctum plug for insertion through the punctal opening of an eye, comprising:

a) a proximal head portion having a lower surface;

b) a distal body portion sized to be received through the punctal opening; and c) a shaft portion provided between said head portion and said body portion, said shaft portion having a longitudinal axis and at least a proximal portion of said shaft having an oblong cross-section perpendicular to said longitudinal axis, wherein said lower surface of said head portion is angled relative to a first plane extending orthogonally through said longitudinal axis, such that said lower surface is angled away from said body portion.

13. A punctum plug according to claim 12, wherein:

said head portion is provided with an oblong cross-section perpendicular to said longitudinal axis.

14. A punctum plug according to claim 13, wherein:

said oblong cross-sections of said head portion and said at least a proximal portion of said shaft have a substantially similar shape.

15. A punctum plug according to claim 14, wherein:

said shape is substantially elliptical.

16. A punctum plug according to claim 12, wherein:

a distal portion of said shaft has a substantially circular cross-section perpendicular to said longitudinal axis.

17. A punctum plug according to claim 12, wherein:

said shaft has a distal portion, and said proximal and distal portions of said shaft meet at an intersection which curves in three dimensions.

18. A punctum plug according to claim 12, wherein:

said head portion has an upper surface provided with a peripheral portion and a central portion, said central portion being one of substantially planar and substantially concave.

19. A punctum plug according to claim 18, wherein:

said peripheral portion of said upper surface is curved toward said lower surface of said head portion.

20. A punctum plug for insertion through the punctal opening of an eye, comprising:

a) a proximal head portion;

b) a distal body portion sized to be received through the punctal opening; and c) a shaft portion provided between said head portion and said body portion, wherein said head portion has a lower surface angled relative to a first plane extending orthogonally through a longitudinal axis of said punctum plug such that said lower surface is angled away from said body portion, and said head portion has a portion provided with an oblong cross-section perpendicular to said longitudinal axis.

21. A punctum plug according to claim 20, wherein:

said head portion has a lower surface angled relative to a first plane extending orthogonally through a longitudinal axis of said punctum plug such that said lower surface is angled away from said body portion.

22. A punctum plug according to claim 20, wherein:

said head portion has an upper surface provided with a peripheral portion and a central portion, said central portion being one of substantially planar and substantially concave.

23. A punctum plug for insertion through the punctal opening of an eye, comprising:

a) a distal plug portion sized to be received at least partially through the punctal opening; and b) a head portion having a proximal head portion with an upper surface and a distal head portion with a lower surface, and having a radial material thickness perpendicular to a longitudinal axis of said punctum plug, wherein said radial material thickness first increases and then decreases when moving along said longitudinal axis from said distal head portion to said proximal head portion.

24. A punctum plug according to claim 23, wherein:

said punctum plug is provided with an axial bore having a bore radius, and at at least one portion of said head portion said radial material thickness is substantially the same as said bore radius.

25. A punctum plug according to claim 23, wherein:

said punctum plug is provided with an axial bore having a bore radius, and at at least one portion of said head portion said radial material thickness is substantially greater than said bore radius.

26. A punctum plug according to claim 23, wherein:

said upper surface of said head portion includes a central portion and a peripheral portion, said central portion being one of substantially planar and substantially concave.

27. A punctum plug according to claim 26, wherein:

said peripheral portion is substantially convex.

28. A punctum plug according to claim 23, wherein:

said distal head portion defines a frustoconical shape.

29. A punctum plug according to claim 23, wherein:

said distal plug portion includes a distal body portion sized to be received through the punctal opening and a proximal shaft portion provided between said head portion and said body portion.

30. A punctum plug according to claim 23, wherein:

said head portion has an axis and an oblong cross-section perpendicular to said axis.

31. A punctum plug according to claim 23, wherein:

said distal plug portion has an axis, and at least a portion of said distal plug portion has an oblong cross-section perpendicular to said axis.

32. A punctum plug for insertion through the punctal opening of an eye, comprising:

a) a head portion having an upper surface, a lower surface, and a substantially cylindrical bore about a longitudinal axis of said punctum plug, said head portion having a directionally normal thickness in a direction normal to said lower surface which changes along said lower surface, and a radial material thickness perpendicular to said longitudinal axis of said punctum plug which first increases when moving along said longitudinal axis from said lower surface toward said upper surface; and b) a distal portion sized to be received at least partially through the punctal opening.

33. A punctum plug according to claim 32, wherein:

said radial thickness, after increasing, decreases when moving along said longitudinal axis from said lower surface toward said upper surface.

34. A punctum plug according to claim 32, wherein:

said distal portion includes a distal body portion sized to be received through the punctal opening and a proximal shaft portion provided between said head portion and said body portion.

35. A punctum plug according to claim 32, wherein:

said punctum plug has an axis, and said head portion has an oblong cross-section perpendicular to said axis.

36. A punctum plug according to claim 32, wherein:

said punctum plug has an axis, and at least a portion of said distal portion has an oblong cross-section perpendicular to said axis.

37. A punctum plug according to claim 32, wherein:

said upper surface includes a central portion about said bore having one of a substantially planar shape and a substantially convex shape.

38. A punctum plug for insertion through the punctal opening of an eye, comprising:

a) a head portion having an upper surface, a lower surface, and a substantially cylindrical bore, said lower surface defining a substantially frustoconical shape; and b) a distal portion sized to be received at least partially through the punctal opening.

39. A punctum plug according to claim 38, wherein:

said punctum plug has a longitudinal axis, a plane extends perpendicular through said longitudinal axis, and said lower surface is angled approximately 15°–25° relative to said plane.

40. A punctum plug according to claim 38, wherein:

said distal portion includes a distal body portion sized to be received through the punctal opening and a proximal shaft portion provided between said head portion and said body portion.

41. A punctum plug according to claim 38, wherein:

said punctum plug has an axis, and said head portion has an oblong cross-section perpendicular to said axis.

42. A punctum plug according to claim 38, wherein:

said punctum plug has an axis and at least a portion of said distal portion has an oblong cross-section perpendicular to said axis.

43. A punctum plug according to claim 38, wherein:

said upper surface includes a central portion about said bore having one of a substantially planar shape and a substantially concave shape.

44. A punctum plug for insertion through the punctal opening of an eye, comprising:

a) a head portion having an upper surface, a lower surface, and a substantially cylindrical bore with a bore radius, said head portion have a radial material thickness about said bore which at at least one portion of said head portion is equal to or greater than said bore radius, and said lower surface defining a substantially frustoconical shape; and b) a distal portion sized to be received at least partially through the punctal opening.

45. A punctum plug according to claim 44, wherein:

said upper surface includes a convex peripheral portion, and a central portion having one of a substantially planar shape and a substantially concave shape.

46. A method for inserting a punctum plug into the punctal opening of an eye, the punctal opening being provided on a surface of the lid margin, said method consisting of:

a) providing a punctum plug defining a longitudinal axis and having a proximal head portion, a distal portion, and a proximal bore substantially coaxial with the longitudinal axis, the head portion having a lower surface and an upper surface, the lower surface being angled relative to a first plane extending orthogonally through the longitudinal axis, the upper surface having a peripheral portion and a central planar portion about the bore which is substantially parallel to the first plane, and the distal portion begin sized to be received at least partially through the punctal opening;

b) placing an insertion tool into the bore of the punctum plug;

c) with the insertion tool, inserting the punctum plug partially through the punctal opening, distal portion first, such that the head portion seats within the punctal opening with a substantial portion of the head portion begin located below the surface of the lid margin; and d) removing the insertion tool from the bore of the punctum plug.

47. A method for inserting a punctum plug into the punctal opening and vertical punctum of an eye, the punctal opening being provided on a surface of the lid margin, said method comprising:

a) providing a punctum plug having a proximal head portion, a distal body portion sized to be received through the punctal opening and having an oblong cross-section with a long axis and a short axis, and a shaft portion provided between the head portion and the body portion, at least a portion of said shaft having an oblong cross-section with first and second lateral axes, the first lateral axis being longer than the second lateral axis, at least the head and shaft portions defining a longitudinal axis and a bore substantially coaxial with the longitudinal axis, the first and second lateral axes being perpendicular to the longitudinal axis, and the long axis of the cross-section of the head being substantially parallel to the first lateral axis of the cross-section through the shaft;

b) placing an insertion tool into the bore of the punctum plug;

c) with the insertion tool, inserting the punctum plug through the punctal opening such that the first lateral axis of the cross-section through the portion of the shaft is provided substantially parallel to the conjunctiva of the eye and such that the head portion seats within the punctal opening with a substantial portion of the head portion being located below the surface of the lid margin.

48. A method according to claim 47, wherein:

the shaft portion includes a proximal portion having the oblong cross-section and a distal portion having a circular cross-section perpendicular to the longitudinal axis.

49. A method according to claim 47, wherein:

the head portion has a lower surface and an upper surface having a peripheral portion and a central planar portion about the bore, the lower surface being angled relative to a first plane extending orthogonally through the longitudinal axis, and the central planar portion of the upper surface being substantially parallel to the first plane.

* * * * *

UNITED STATES PATENT AND TRADEMARK OFFICE
CERTIFICATE OF CORRECTION

| | | |
|---|---|---|
| PATENT NO. | : 6,027,470 | Page 1 of 1 |
| APPLICATION NO. | : 09/095194 | |
| DATED | : February 22, 2000 | |
| INVENTOR(S) | : Richard W. Mendius | |

It is certified that error appears in the above-identified patent and that said Letters Patent is hereby corrected as shown below:

Title page, Item [54] and Column 1, line 3,

Title, "PUNCTUAL" should be --PUNCTAL--

Signed and Sealed this

Fifth Day of June, 2007

JON W. DUDAS
*Director of the United States Patent and Trademark Office*